United States Patent [19]

Pigerol et al.

[11] 3,958,011

[45] May 18, 1976

[54] COMPOSITIONS OF TRI-N-PROPYLACETIC ACID AND SALTS THEREOF AND TREATMENT OF NEUROLOGICAL DISORDERS WITH SUCH COMPOSITIONS

[75] Inventors: Charles Pigerol, St. Ouen; Pierre Luc Eymard, Fontaine, both of France

[73] Assignee: Labaz, Paris, France

[22] Filed: Mar. 31, 1975

[21] Appl. No.: 563,809

Related U.S. Application Data

[63] Continuation-in-part of Ser. No. 426,730, Dec. 13, 1973.

[30] Foreign Application Priority Data

Dec. 11, 1972 France .............................. 72.43946

[52] U.S. Cl. ............................................... 424/320
[51] Int. Cl.$^2$ ......................................... A61K 31/16
[58] Field of Search ................................... 424/320

[56] References Cited
OTHER PUBLICATIONS

Chem. Abst., Vol. 51, Subj. Index J-Z pp. 2510$^s$–2511$^s$ and Vol. 51–8693h(1957).

Primary Examiner—Stanley J. Friedman
Attorney, Agent, or Firm—Mason, Kolehmainen, Rathburn & Wyss

[57] ABSTRACT

Tri-n-propylacetic acid and its alkali metal salts are useful in the treatment of central neurological troubles due to or accompanied by cerebral ischemia and as tranquillizers.

6 Claims, No Drawings

COMPOSITIONS OF TRI-N-PROPYLACETIC ACID AND SALTS THEREOF AND TREATMENT OF NEUROLOGICAL DISORDERS WITH SUCH COMPOSITIONS

CROSS-REFERENCE TO RELATED APPLICATION

This application is a continuation-in-part of our co-pending application Ser. No. 426,730 filed Dec. 13, 1973.

This invention relates to tri-n-propylacetic acid of formula:

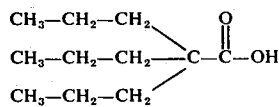

and its alkali metal salts such as the lithium, sodium and potassium salts for use in the treatment of central neurological disorders.

These compounds may all be prepared by known processes such as the following:

a. Tri-n-propylacetic acid is obtained by treating tri-n-propylacetamide with butyl nitrite in an acid medium, preferably hydrochloric, acid, as described in J. Amer. Chem. Soc. 70,3091 (1948)

b. The alkali metal salts of tri-n-propylacetic acid are obtained by treating tri-n-propylacetic acid with the appropriate alkali metal hydroxide.

The invention also relates to pharmaceutical or veterinary compositions containing as active principle at least one compound selected from the group comprising tri-n-propylacetic acid and its alkali metal salts, in association with an appropriate carrier.

Pharmacological trials carried out on experimental animals have shown that the compounds of the invention possess properties which are of considerable value in the treatment of pathological conditions due to disturbances of the central nervous system and disorders relating to the field of neuropsychiatry. These pharmacological trials, which will be described in detail, have revealed that the compounds of the invention can act as anticonvulsants, antianoxics, regulators of the central nervous system, myorelaxants and tranquillizers.

As a result of these findings, the compounds of the invention can constitute particularly valuable agents for the treatment of various kinds of central neurological disturbances due to or accompanied by cerebral ischemia.

As an example of such central neurological disturbances or of disorders induced by central neurological dysfunction, the following may be cited: convulsive states and seizures such as, for example, epilepsy, difficulties with respect to memory, equilibrium and fixing the attention, as well as dizzeness, decrease of arterial pressure, cephalalgia and comatose states.

It is, therefore, another object of the invention to provide a method for treating central neurological disorders due to a accompanied by cerebral ischemia and including in particular convulsive states and seizures, in a host in need of such treatment, comprising administering to said host an effective dose of at least one compound selected from the group consisting of tri-n-propylacetic acid and its alkali metal salts.

Irrespective of the dosage form used, the total daily dosage of the active principle should be in the range of about 200 mg to 1200 mg with single doses ranging from about 50 mg to about 1000 mg.

The compounds of the invention are all known compounds inasmuch as they are covered by the general formula of British Patent No. 760,114 relating to substances capable of reducing the level of cholesterol in the blood.

However, there is nothing in the said British Patent which could even remotely suggest the particular activities which, in the light of present knowledge, can be attributed to the compounds of the invention.

In the field of diseases riquiring anticonvulsant therapy and, in particular, epilepsy, there are numerous drugs of undeniable efficacy. However, these classical substances, such as the barbiturates and molecules of similar structure cause an overall depression of the central nervous system, which, moreover, explains their anticonvulsant activity.

For this reason, such drugs frequently cause undesirable sideeffects, such as difficulty in fixing the attention, reduction in intellectual efficiency and somnolence as well as biological disorders of which the most serious are haematological.

The compounds of the invention do not present these disadvantages since they do not act by provoking a general depression of the central nervous system.

Furthermore, certain well-known anticonvulsant agents are toxic at relatively low doses while others are only useful for the treatment of one single type of epilepsy.

Again, the compounds of the invention do not present these disadvantages since they are relatively non toxic and at the same time they possess a very wide range of properties which are likely to render them useful in the treatment of an extremely broad variety of convulsive states and more particularly most clinical forms of epilepsy.

Furthermore, the antianoxic properties of the compounds of the invention will be extremely useful, more particularly for preventing convulsive seizures since it is well known that anoxia can induce such seizures.

In addition the antianoxic properties in question will also be extremely valuable for delaying the occurrence of cerebral pain due to oxygen deficiency namely cerebral ischemia.

Cerebral ischemia can be provoked by numerous causes such as, for example: cerebral vascular diseases due to senescence, thrombosis or tumors. At present in the case of cerebral vascular diseases and their resulting disturbances such as central neurological disorders and their consequences, cerebral vasodilators are commonly used. However, such drugs must be employed in accordance with the cerebral state of the patient.

Since these compounds act by mechanical means namely by dilating the arterioles to increase the blood flow and consequently the amount of oxygen in the brain, they will be ineffective, for example in cases involving arteriosclerosis.

The compounds of the invention, on the other hand do not present this disadvantage as they do not act by mechanical means but exert their effect directly on the metabolism of the nervous cells without affecting the conditions of irrigation. The compounds of the invention will be thus likely to constitute very useful antianoxic agents particularly in cases where the classical drugs are ineffective.

From the point of view of tranquillizing activity, the compounds of the invention are not put forward as possessing tranquillizing properties which are superior to those of the best agents so far known. However, it should be noted that the compounds of the invention, while being endowed with an appreciable tranquillizing action, also present a wide variety of neurotropic properties exceeding those of existing tranquillizers.

Finally, it should be emphasized that the use of the compounds of the invention is not accompanied by the indesirable side-effects of the neuroleptic and anti-depressant agents such as, for example, extra-pyramidal disturbances with the neuroleptics and complete reversals of mood with both types of agents. On the contrary, the compounds of the invention exert their effect at doses considerably lower than those required to provoke disturbances of behaviour.

The following is an account of the pharmacological trials which have been undertaken with a view to determining the toxicity of the compounds of the invention and the presence of the various properties which, taken together, are capable of rendering the said cmpounds useful as anticonvulsants, antianoxics, regulators of the central nervous system, myorelaxants and tranquillizers.

1. ACUTE TOXICITY

The $LD_{50}$ was determined on the mouse by intraperitonel route using the technique of KARBER and BEHRENS. The result obtained for sodium tri-n-propylacetate was 327 mg/kg which corresponds to a dose 20 to 80 times the daily therapeutic dose of the compound in question.

Under the same conditions, the $LD_{50}$ of a tranquillizer i.e. diazepam was found to be 55 mg/kg.

These results show that sodium tri-n-propylacetate is much less toxic than diazepam.

2. NEUROTOXICITY

The test used was that known as the rota rod test (BOISSIER-Therapie 1958, XIII, pp. 1074–1118). This test aims at enabling the animals' ability to coordinate their movements to be evaluated. It is carried out on batches of 10 mice each weighing about 25 g. The compound to be tested is administered by intraperitoneal route to the animals of each batch so that each batch receives a higher dose than that given to the preceding batch. Thirty minutes after administration, the mice are placed for two minutes on a wooden roller of 4.8 cm diameter which turns at the rate of 4 revolutions per minute. The roller has a rough surface to prevent the animals from slipping.

By this means, the neurotoxic dose 50 (NTD 50) can be determined, i.e. the dose of the compound with which one half of the animals can no longer stay on the roller during the period of time fixed as the reference period.

The result obtained with the preferred compound of the invention namely sodium tri-n-propylacetate was a NTD 50 of 120 mg/kg.

The value of this test is twofold. Failure on the part of the animals gives a very early indication of the slightest damage to the neuromuscular functions which cannot be discerned by any other means. Secondly, this test serves as an element of comparison for drawing up index figures involving the results obtained with other behaviour tests.

3. ANTICONVULSANT ACTION

The anticonvulsant action was first studied by the method involving a pentylenetetrazol-induced seizure and then by the maximum electroshock seizure technique.

a. Pentylenetetrazol-induced seizure

The purpose of this test which is carried out on mice is to determine whether the compounds of the invention, when given preventively by intraperitoneal route, are capable at certain doses of protecting some of the animals against the epileptic seizure produced by an adequate and predetermined dose of pentylenetetrazol which would be 100% fatal in the absence of the compound. The test was carried out on batches of 10 male OF 1 mice weighing about 25 g. Each batch of animals received an intraperitoneal dose of the compound to be studied so that each batch received a higher dose than the preceding batch. Seven-and-a-half minutes after administration, the animals were each given 125 mg/kg of pentylenetetrazol by intraperitoneal route. The experiment was repeated 15 minutes and 30 minutes after administration of the compound under study and the number of deaths was noted 3 hours after administration of the pentylenetetrazol. From these findings, the effective dose 50 or $ED_{50}$ was calculated by the method described by LITCHFIELD and WILCOXON in J. Pharmacol. 1938, 2 p. 192– 216.

The results obtained with compounds of the invention are given in the following Table:

TABLE I

| Compound | Time after administration | | |
|---|---|---|---|
| | 7 min. 30 sec | 15 min. | 30 min. |
| Sodium tri-n-propyl-acetate $ED_{50}$ in mg/kg | 78 | 66 | 110 |
| Tri-n-propylacetic acid $ED_{50}$ in mg/kg | 87 | 72 | 124 | b. Maximum electroshock seizure

This seizure is characterized in the mouse by extension of the back paws for 5 to 10 seconds. The extension is similar to that observed during the tonicoclonic seizures provoked by chemical convulsants such as pentylenetetrazol or strychnine.

The test was carried out on batches of 10 mice of the OF 1 strain weighing about 22 g. Various doses of the compound to be tested were administered by intraperitoneal route so that each batch of animals received a higher dose than that given to the preceding batch. Fifteen minutes later, each animal received an electric shock of twice threshold intensity (about 60 volts). The number of tonic seizures was noted and the $ED_{50}$ was calculated, i.e. the dose of the compound under study required to protect 50% of the animals against tonic seizures.

The following results were obtained for the preferred compounds of the invention and for phenobarbital:

| Compound | $ED_{50}$ in mg/kg |
|---|---|
| Sodium tri-n-propylacetate | 130 |
| Tri-n-propylacetic acid | 145 |

| Compound | -continued $ED_{50}$ in mg/kg |
|---|---|
| Phenobarbital | 78 |

The efficacy index of the compounds was also calculated by comparing the $ED_{50}$ with the dose required to obtain a hypnotic effect in 50% of the animals. This latter value is indicated by the symbol $HD_{50}$ or hypnotic dose 50 and the efficacy index by the fraction:

$$\frac{HD_{50}}{ED_{50}}$$

The efficacy indices of sodium tri-n-propylacetate and of phenobarbital were found to be as follows:

| Sodium tri-n-propylacetate | 1.0 |
|---|---|
| Phenobarbital | 1.3 |

These figures show that sodium tri-n-propylacetate presents an index which is slightly less favorable that that of phenobarbital. However, sodium tri-n-propylacetate does not have the disadvantages of the barbiturates and exerts its effect at a dose well below its $LD_{50}$.

4. MYORELAXANT PROPERTIES

The myorelaxant properties of the compounds of the invention were determined by the traction test described by COURVOISIER (Psychotropic Drugs, Milan 1957, pp 373–391).

Traction Test

This test enables sense of balance as well as muscular tonus and strength to be evaluated.

The test is carried out on groups of 10 male mice of the OF 1 strain weighing about 25 g. It consists of suspending the mice by the front paws to a horizontally stretched wire. Note is first taken of the time required by a group of control animals to effect recovery i.e. to place at least one of their back paws on the wire. Each batch of animals is then given an intraperitoneal dose of the compound to be studied so that each batch receives a higher dose than the preceding batch. Note is then taken of the number of animals which have lost the traction reflex 15, 30 and 45 minutes after administration of the compound and at the end of each period the $ED_{50}$ is calculated i.e. the dose of the compound under study which causes loss of the reflex in 50% of the animals.

The results obtained with sodium tri-n-propylacetate are listed in the following Table:

Table II

| Dose in mg/kg | Time after administration | | |
|---|---|---|---|
| | 15 min. | 30 min. | 45 min. |
| 0 | 0 | 0 | 0 |
| 20 | 1 | 2 | 0 |
| 50 | 0 | 1 | 2 |
| 75 | 3 | 0 | 1 |
| 100 | 8 | 1 | 0 |
| 150 | 10 | 10 | 9 |
| $ED_{50}$ in mg/kg | 80 | 110 | 130 |

These figures show that as a myorelaxant the activity of sodium tri-n-propylacetate is at its maximum 15 minutes after administration by intraperitoneal route.

In order to obtain an activity index figure 30 minutes after administration the rota rod test described above was also performed using for comparison a known myorelaxant, namely mephenesin.

The following results were recorded:

| | Sodium tri-n-propylacetate | Mephenesin |
|---|---|---|
| $NTD_{50}$ in the rota rod test in mg/kg | 120 | 100 |
| $ED_{50}$ in the traction test in mg/kg | 110 | 250 |
| Activity index: $\frac{NTD_{50}}{ED_{50}}$ | 1.1 | 0.4 |

These figures show a very favorable activity index for sodium tri-n-propylacetate as compared with the activity index of a known myorelaxant. It is seen, in fact, in the case of sodium tri-n-propylacetate, that the myorelaxant dose is reached before the $NTD_{50}$ whereas in the case of mephenesin the $NTD_{50}$ is very much lower than the myorelaxant dose.

5. HYPNOTIC PROPERTIES

The hypnotic properties of the compounds of the invention were demonstrated by studying posture reflex.

Male mice of the OF 1 strain, weighing about 25 g. were divided into batches of 10. The animals of each batch were given an intraperitoneal dose of the compound to be studied so that each batch received a higher dose than the preceding batch.

The numbers of animals which lost the reflex at various times after administration were noted.

In this way, the $HD_{50}$ at different times after administration was determined i.e. the dose of the compound under study which caused 50% of the animals to lose the posture reflex at a given time after administration.

The results recorded with sodium tri-n-propylacetate are given in the following Table:

Table III

| Compound | Time after administration | | | |
|---|---|---|---|---|
| | 15 min. | 30 min. | 45 min. | 60 min. |
| Sodium tri-n-propyl-acetate $HD_{50}$ in mg/kg | 120 | 130 | 150 | 200 |

6. TRANQUILLIZING PROPERTIES

The tranquillizing properties of the compounds of the invention were demonstrated by the chimney test, the evasion test and the hole-board test described by BOISSIER in Med. Exp. 1960, 3, pp 81–84, Therapie 1965, XX, pp. 895–905 and Therapie, 1964, XIX, pp. 571–589 respectively.

a. Chimney test

This test enables two groups of factors to be evaluated namely neuromuscular factors (muscular strength, agility, coordination of movements) and psychological factors (curiosity, fright, flight instinct).

It was carried out on batches of 10 mice weighing about 25 g each. The compound to be studied was given to each batch by intraperitoneal route so that each batch received a higher dose than the preceding batch. The mice were placed, one after another, head first in a test-tube 30 cm long and calibrated in accordance with the size of the mouse so that by moving backwards the animal could get out of the tube in less than 30 seconds. The number of animals which were unable to do this was noted.

In this way, the $ED_{50}$ could be determined i.e. the dose of the compound at which 50% of the animals failed to get out of the test-tube within the 30-second period.

The result obtained with sodium tri-n-propylacetate was 72 mg/kg.

These tranquillizing effects were obtained at only about half the doses required to modify neuromuscular functions in the rota rod test.

b. Evasion test

This test enables the exploring capacities of mice to be studied. A parallelepipedic lidless plywood box is used which contains an inclined plane, also of plywood, covered with a fine mesh. A horizontal datum line is marked on the inclined plane 2 cm below the point at which the plane bears on the box edge. The whole device is placed in an artificially lit room away from all shrill noise. Any crossing, in an upward direction, by a mouse of the datum line is termed an "exit".

The test was carried out on batches of 28 mice weighing about 22 g. The animals of each batch received an intraperitoneal dose of the compound to be studied so that each batch received a higher dose than the preceding batch.

Thirty minutes after administration of the compound, the animals were placed in the box by batches and kept at the bottom for 10 seconds by a movable board. The average length or time after which the first exit occurred was noted as well as the total number of exits per batch every minute for 5 minutes. The same details were also recorded for a control batch which had not received the compound. The following results were obtained with the preferred compound of the invention namely sodium tri-n-propylacetate:

Table IV

| Compound | Total number of exits per batch | | | | | Average time before first exit in seconds |
|---|---|---|---|---|---|---|
| | 1 min. | 2 min. | 3 min. | 4 min. | 5 min. | |
| Controls | 48 | 50 | 43 | 38 | 42 | 14 |
| Sodium tri-n-propyl acetate 50 mg/kg | 54 | 44 | 43 | 41 | 28 | 25 |
| Sodium tri-n-propyl acetate 75 mg/kg | 44 | 37 | 31 | 34 | 28 | 21 | c. Hole-board test

This test enables a quantitative evaluation to be made of the exploring capabilities of mice in relation to their curiosity. The material comprises a board 40 cm × 40 cm and 1.7 cm thick in which 16 holes, 3 cm in diameter, have been cut. The board is placed upon four legs sufficiently high (1.5 m) for the holes to appear bottomless to the animals. The experiment is carried out in as great a silence as possible.

The test was performed on batches of 10 male OF 1 mice weighing about 23 g. The animals of each batch were given an intraperitoneal dose of the compound to be tested so that each batch received a higher dose than the preceding batch. The control group did not receive any of the compound under study. Thirty minutes after administration, each batch was placed in the middle of the board and the total number of holes explored by each batch was noted every minute for 5 minutes.

The results obtained with sodium tri-n-propylacetate are given in the following Table:

Table V

| Compound | Total number of holes explored | | | | |
|---|---|---|---|---|---|
| | 1 min. | 2 min. | 3 min. | 4 min. | 5 min. |
| Controls | 32 | 35 | 32 | 43 | 33 |
| Sodium tri-n-propyl acetate 50 mg/kg | 15 | 13 | 14 | 19 | 17 |
| Sodium tri-n-propyl acetate 75 mg/kg | 2 | 6 | 3 | 1 | 7 |

The above results show that sodium tri-n-propylacetate tends to reduce the animals' curiosity.

7. NEUROLEPTIC PROPERTIES

All the catalepsy tests carried out on the rat (crossing of homolateral paws, four corks test, parallel bars test) with the compounds of the invention gave negative results with doses just below the hypnotic doses.

8. ANTIANOXIC PROPERTIES

Action on the anoxic seizure induced by gallamine triiodoethylate

The injection of a sufficient dose of a synthetic curariform substance such as gallamine triiodoethylate provokes in the rat paralysis of the diaphragm. The animal then dies by asphyxia.

Male rats of the OFA strain and weighing about 250 g. were first anesthetized with ether in order to enable tracheotomy to be performed and cortical electrodes to be inserted. Each rat was then maintained under conditions of artificial respiration by means of an appropriate apparatus and a paralysing dose of gallamine triiodoethylate was administered by intraperitoneal route to eliminate spontaneous breathing. The electrocorticogram, the electrocardiogram and the rectal temperature were registered. After a period of 30 minutes during which stabilization of the registrations was obtained the animal was treated with 2 millimols/kg of an oily solution of tri-n-propylacetic acid or an aqueous solution of one of its alkali metal salts. The artificial respiratory apparatus was stopped 5 minutes after treatment and note was taken of the cardiac frequency every 10 seconds as well as of the period of time between the stopping of the apparatus and the appearance of the flat tracing on the electrocorticogram. This period of time represents the period of survival of the animal. The value of the cardiac frequency corresponding to moment of appearance of the flat tracing was calculated by extrapolation.

The same test was performed on control animals but without administration of a compound of the invention.

The results obtained with tri-n-propylacetic acid and its sodium salt are given in the Table which follows:

Table VI

|  | Control animals | Tri-n-propylacetic acid or its sodium salt |
| --- | --- | --- |
| Period of survival in seconds | 74.3 ± 2.3 | 87.9 ± 3.7 |
| Rectal temperature | 32.6 ± 0.4 | 33.3 ± 0.3 |
| Cardiac frequency when the flat tracing appears | 150 | 109 |

These results show that tri-n-propylacetic acid or its sodium salt is capable of producing an increase of the period of survival in the animals so treated in comparison with the controls. In the above case the period of survival of the treated animals is 19% greater than that of the controls. It is also clear from the above Table that the antianoxic effect so produced is not caused by cardiac interference. On the contrary, the bradycardiac effect observed in the treated animals induces the rapid appearance of the flat tracing in the electrocorticogram and antagonizes, in this manner the antianoxic action of the compounds under study.

The therapeutic compositions of the invention may be presented in any form suitable for administration in human or veterinary medicine. The unit of administration may be in the form of, for example, a coated- or uncoated-tablet, a soft- or hard-gelatin capsule, an ampoule or syrup for oral administration, of a sterile solution for parenteral administration and of a suppository for rectal administration.

According to the type of administration unit chosen, the therapeutic compositions fo the invention will be prepared by associating at least one of the compounds of formula I with an appropriate excipient, the latter being composed, for example, of at least one ingredient selected from amongst the following substances: talc, magnesium stearate, milk sugar, saccharose, carboxymethylcellulose, starches, kaolin, levilite, cocoa-butter.

The preparartion of the compounds of the invention together with therapeutic compositions containing them are illustrated by the following non-limitative Examples:

EXAMPLE 1

Preparation of tri-n-propylacetic acid

In a flask equipped with a dropping-funnel were placed 480 g. of distilled dioxan followed by 80 g. (0.432 mol) of tri-n-propylacetamide which was dissolved by stirring. For a period of 20 minutes a current of dry hydrochloric acid gas was passed through the dioxan solution at room-temperature, which represented a total of 100 g of hydrochloric acid gas. At the end of this operation, 88 g (0.86 mol) of freshly distilled butyl nitrite was slowly added over a period of 2 hours through the dropping-funnel. The temperature of the reaction medium rose from 31° to 43°C which necessitated cooling in a water-bath. The solution was then maintained for 2 hours at 85°–90°C. The dioxan was distilled off under a reduced pressure of 20 mm. Hg and a pasty residue obtained at room-temperature. This residue was dissolved in 290 g of a 10% aqueous solution of potassium hydroxide. The aqueous layer was decanted out and extracted twice with 75 g of ethyl ether. The potassium solution was acidified with 118 g of a 36% solution of hydrochloric acid (at 10°/20°C) after which the oily phase was decanted out. The aqueous phase was extracted twice with 75 g of ethyl ether after which the oily phase and the ethereal extracts were placed together. The ethereal solution was washed twice with 100 g of water and dried for 24 hours over 100 g of anhydrous sodium sulphate. The sodium sulphate was then centrifuged out. The ethyl ether was distilled off under atmospheric pressure and the residue recuperated under 7 mm. Hg. The fraction obtained boiled at 126° to 128°C and crystallized rapidly. In this way, 61 g of crude tri-n-propylacetic acid were obtained, which represents a yield of 76%. The crude product was then dissolved by heating in 75 g of ethyl ether. The ethereal solution was filtered while hot and the filtrate left at a temperature of −30°C for 4 hours. The precipitate which formed was centrifuged out and dried in a desiccator under a reduced pressure of 20 mm. Hg for 6 hours. By this means, 46 g of pure tri-n-propylacetic acid were obtained which represents a yield in pure product of 75.4% and a total yield of 57.3% M.P. 67°C

EXAMPLE 2

Preparation of sodium tri-n-propylacetate

In a flask equipped with a dropping-funnel and a mechanical stirrer were placed 30 g (0.161 mol) of pure tri-n-propylacetic acid prepared as described above and 75 g of toluene. The mixture was stirred until dissolution after which a hot solution of 6.45 g of sodium hydroxide in 30 g of Methanol was added through the dropping-funnel. To the solution thus obtained was added 1g of CECA WSL black after which the whole was refluxed for 1 hour while being stirred. The black was filtered off and the residual mixture was distilled by adding little-by-little through the dropping-funnel 88 g of toluene to prevent the mixture from forming a mass. Distillation was suspended when the temperature at the head of the column reached 105°C, after which the mixture was cooled to room-temperature The precipitate which formed was centrifuged out and rinsed twice with 20 g of acetone. It was then dried in a rotatory evaporator at 80°C for 2 hours and then at 105°C under atmospheric pressure in a ventilated drying-oven for 4 hours. In this way, 30 g of sodium tri-n-propylacetate were obtained which represents a yield of 89.5%.

EXAMPLE 3

Soft-gelatin capsules corresponding to the following formulation were prepared by known pharmaceutical techniques:

| Ingredient | mg per capsule |
| --- | --- |
| Sodium tri-n-propylacetate | 150 |
| Talc | 15 |
| Magnesium stearate | 2 |
|  | 167 |

EXAMPLE 4

Suppositories corresponding to the following formulation were prepared by known pharmaceutical techniques:

| Ingredient | mg per capsule |
| --- | --- |
| Sodium tri-n-propylacetate | 200 |
| Glycocoll | 200 |

-continued

| Ingredient | mg per capsule |
|---|---|
| Cocoa-butter | 1600 |
| | 2000 |

We claim:

1. A method for treating central neurological disorders due to or accompanied by cerebral ischemia in a host in need of such treatment comprising administering to said host an effective dose of a compound selected from the group comprising tri-n-propylacetic acid and an alkali metal salt thereof.

2. A method as defined by claim 1 wherein the compound is tri-n-propylacetic acid.

3. A method as defined by claim 1 wherein the compound is sodium tri-n-propylacetate.

4. A method as defined by claim 1 wherein the central neurological disorders are convulsive states and seizures.

5. A method as defined by claim 4 wherein the convulsive states and seizures are epileptic.

6. A method as defined by claim 1 wherein the effective dosage is in the range of 200 mg to 1200 mg per day.

* * * * *